United States Patent [19]

McCaughan, Jr.

[11] Patent Number: 4,693,556
[45] Date of Patent: Sep. 15, 1987

[54] APPARATUS FOR PRODUCING A SPHERICAL PATTERN OF LIGHT AND METHOD OF MANUFACTURE

[75] Inventor: James S. McCaughan, Jr., Galena, Ohio

[73] Assignee: Laser Therapeutics, Inc., Worthington, Ohio

[21] Appl. No.: 741,144

[22] Filed: Jun. 4, 1985

[51] Int. Cl.⁴ .................. G02B 6/00; A61B 17/36; F21V 7/04; B32B 31/00
[52] U.S. Cl. .................... 350/320; 350/96.10; 350/96.15; 350/96.18; 350/96.20; 128/303.1; 128/395; 128/397; 362/32; 156/272.2; 156/272.8
[58] Field of Search ............... 350/96.10, 96.15, 96.18, 350/96.20, 96.24, 96.29, 96.30, 320; 362/32; 128/303.1, 362, 395, 397; 156/272.2, 272.8, 275.3, 275.7

[56] References Cited

U.S. PATENT DOCUMENTS

| 3,439,157 | 4/1969 | Myles | 362/32 |
| 3,589,800 | 6/1971 | Cardona | 350/96.26 |
| 4,193,663 | 3/1980 | Timmermann | 350/96.18 |
| 4,516,022 | 5/1985 | Lindgren | 350/96.10 |
| 4,660,925 | 4/1985 | McCaughan, Jr. | 350/96.15 |

OTHER PUBLICATIONS

Russo et al., "Lens-Ended Fibers for Medical Applications . . . ", Applied Optics vol. 23, No. 19, 10/84, pp. 3277-3283.

Primary Examiner—William L. Sikes
Assistant Examiner—Brian M. Healy
Attorney, Agent, or Firm—George Wolken, Jr.

[57] ABSTRACT

The present invention discloses an optical radiating apparatus constructed on one end of a light-conducting optical fiber such that, upon encountering this radiator, light is caused to leave the fiber and radiate in a spherical pattern with respect to the end of the fiber. This optical radiator is constructed such that the pattern of radiated light is nearly uniform in intensity in a spherical pattern, without areas of light intensity significantly different from the average distribution around the surface of a sphere. The present invention also discloses a method to manufacture the above-described light radiating apparatus, ensuring uniformity of light intensity and the ability to transmit relatively intense light without developing regions of optical, thermal or mechanical damage.

1 Claim, 3 Drawing Figures

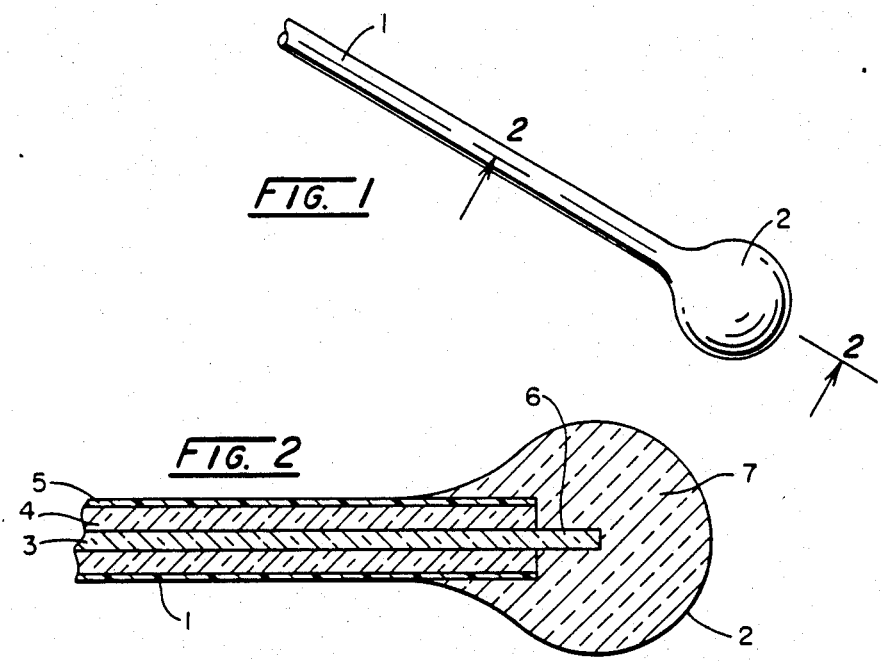
FIG. 1
FIG. 2
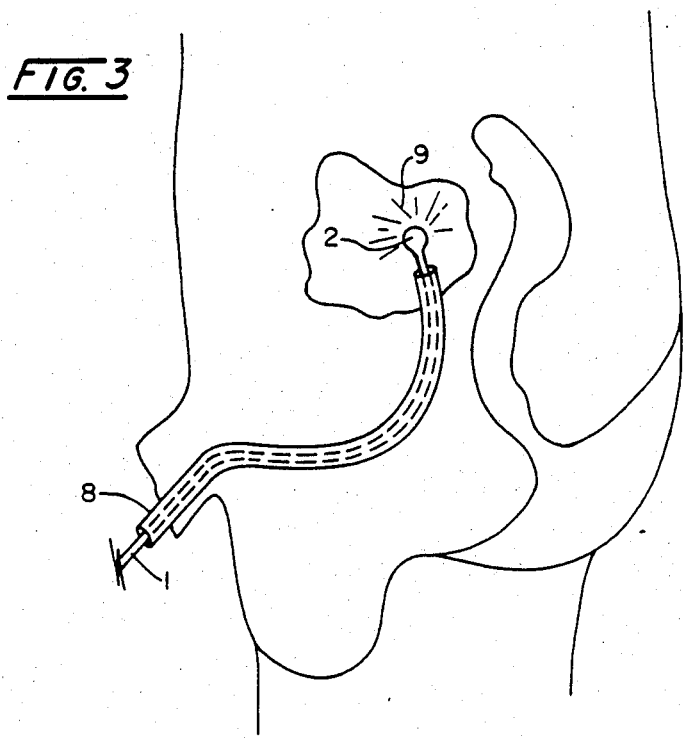
FIG. 3

APPARATUS FOR PRODUCING A SPHERICAL PATTERN OF LIGHT AND METHOD OF MANUFACTURE

BACKGROUND OF INVENTION

This invention relates to a fiber optic device and more particularly to a device for dispersing light propagating along an optical fiber into an approximately uniform spherical pattern surrounding the fiber, and a method to manufacture this device.

During the course of the last several years, a new method of treatment for cancer in humans has been receiving considerable attention. Known as "photodynamic therapy" (PDT), this treatment makes use of two well-documented effects to destroy cancerous tissues. The two effects are: (1) the propensity of certain chemicals to concentrate or remain preferentially in cancer cells, and (2) the ability of light with a specific wavelength to promote photochemical reactions which, in the absence of such light, would proceed extremely slowly or not at all. The first effect is the foundation of the entire field of chemotherapy in which more or less "poisonous" chemicals are introduced into the patient. It is desired that lethal doses of the chemical concentrate in the cancer cells while non-lethal doses are received by normal cells. The second effect underlies the entire field of photochemistry in which light promotes many reactions not otherwise occurring. The fields of photography, photosynthesis, vision, etc. are common examples of light causing chemical reactions to proceed.

PDT combines these two effects in the treatment of cancer. A mixture of chemicals known as "hematoporphyrin derivative" (HpD) is widely known to reamin preferentially in cancer cells. As extracted from serum, HpD fluoresces when exposed to light. This has proven to be a valuable diagnostic tool for many kinds of cancer. However, it has also been observed that, when illuminated with light of a specific wavelength and in sufficient intensity, HpD undergoes a photochemical reaction and kills the cell in which it resides. The exact nature of the chemical reaction which leads to the death of the host cell is not precisely defined and is the subject of continuing research at many institutions. However, the effect of killing the host cell is well-documented and is finding increasing use as a cancer treatment in the U.S. and elsewhere.

In use, a patient is injected with HpD in a appropriate dosage as determined by the attending physician. The HpD permeates cells throughout the body, but dissipates from normal cells much more rapidly than from cancer cells. Typically, 48 to 72 hours after injection, there is a substantially greater concentration of HpD in cancer cells relative to the adjacent normal tissue. Thus, exposing the cancerous 25 region during this sensitive period to suitable light (for HpD this is red light with wavelength close to 630 nanometers) of sufficient intensity (as determined by the physician considering such things as the depth of 1 the tumor, its nature, location, orientation etc.) will lead to preferential destruction of the cancerous tissues exposed to light.

PDT has several attractive features. HpD by itself is not a "poison". Thus, unlike much conventional chemotherapy, the patient has virtually no discomforting side effects from the treatment. (However, the patient is overly sensitive to light and is advised to stay out of sun light for several weeks following treatment.) PDT does not intefere with other modes of treatment. It can be readily used as part of a whole range of treatments the physician may prescribe for the patient. Most attractive of all, PDT is the first definite example of a method of cancer treatment combining photochemistry with preferential concentration in cancer cells. Since both effects are known to be widespread, HpD will almost certainly not be the last treatment to work in this manner.

However, some problems remain with PDT. The treatment is not effective unless suitable intensity of light is brought to bear upon the tumor. Thus, for cancers that rapidly spread over great areas, rapidly invade tissues deeply, or otherwise cannot be reached with light, PDT may not be the method of choice for the physician.

The present invention concerns a device which allows the physician to effectively deliver intense light to certain tumor sites not otherwise conveniently reached. The device must be capable of carrying intense radiation without overheating and destroying itself. The device must provide a uniform pattern of illumination so the physician can irradiate the entire treatment area with intense radiation lethal to the cancer cells, without leaving "dark areas" of undestroyed cells to cause future problems for the patient.

For cancers occurring in cavitary regions of the body, the appropriate pattern of radiation for treatment is a uniform spherical pattern. Thus, for PDT treatment of bladder cancer, an optical fiber is required to be equipped with an apparatus at one tip that disperses light propagating along the fiber in a uniform spherical pattern. This optical radiating apparatus must produce a reasonably uniform pattern of light, so the physician can have reasonable confidence in his applied dosage level. The apparatus must also be able to transmit reasonably intense radiation for effective treatment without developing "hot spots", optical, thermal or mechanical damage. Finally, the apparatus must perform these tasks in an environment in which it encounters blood, mucus, extraneous bits of tissues, and other substances which may contaminate its optical properties. Such an optical radiating apparatus for producing a uniform spherical pattern of light, and a method for manufacturing such an apparatus, is the subject of the present invention.

SUMMARY AND OBJECTS OF THE INVENTION

The present invention discloses an optical radiating apparatus constructed on one end of a light-conducting optical fiber such that, upon encountering this radiator, light is caused to leave the fiber and radiate in approximately spherical pattern with respect to the central axis of the fiber. This optical radiator is constructed such that the pattern of radiated light is nearly a uniform spherical shape. Also the light is dispersed around this spherical pattern in a nearly uniform intensity distribution, without areas of light intensity significantly different from the average distribution on the surface of the sphere. The above properties are achieved without the need to reshape the cylindrical core of the optical fiber.

The present invention also disclose a method to manufacture the above-described light radiating apparatus. For the intended use in cancer treatment, significant light intensity must be carried by the optical fiber and the radiating apparatus without developing "hot spots" and burn regions, to the possible detriment of the patient. The radiating apparatus must maintain its structural integrity and uniform spherical pattern of radiated light in an environment of mucus, blood, tissue and other substances encountered in the treatment of a patient.

Thus, a primary object of the present invention is to provide an apparatus for producing a uniform spherical pattern of light at the tip of an optical fiber.

Another object of the present invention is to provide a uniform optical radiator as described, in a configuration suitable for use in patients.

Another object of the invention is to provide an optical radiator able to disperse relatively intense radiation without suffering optical, thermal or mechanical damage.

Another object of the present invention is to provide a method of manufacturing the optical radiator with the properties described in a reliable, and reproducable fashion, without the necessity of reshaping the core of the optical fiber from its usual cylinderical shape.

BRIEF DESCRIPTION OF DRAWINGS

FIG. 1: A perspective view of the optical radiating apparatus on the tip of an optical fiber.

FIG. 2: Cross-sectional view of the optical radiating device as mounted on the tip of an optical fiber, viewed as a section through the central axis of the optical fiber (noted 2 in FIG. 1).

FIG. 3: Cut-away view of a male patient's pelvis with the present invention inserted into the bladder through a flexible tube.

DESCRIPTION OF THE PREFERRED EMBODIMENTS

FIG. 1 shows in perspective view a typical optical fiber, 1, conducting light from the upper left portion of the figure into the region of an optical radiating apparatus, 2. This radiating apparatus surrounds one terminus of the optical fiber 1. The apparatus 2 is the subject of the present invention. It disperses light propagating along optical fiber 1 into an approximately uniform spherical pattern. Apparatus 2 is typically small enough to insert into a patient, frequently through a tube into the bladder or rectum or into other regions of the body where approximately spherical patterns of light are required. Another property required of radiating apparatus 2 is that it withstand the relatively high intensities of light it must carry. Typically, up to about 200 milliwatts per sq. cm. of 630 nanometer radiation must be delivered to the tumor. Thus, the fiber and the optical radiating apparatus should be able to withstand up to a few watts of power without suffering significant optical, thermal or mechanical damage even when used in vivo.

FIG. 2 shows in cross-sectional view the optical fiber terminating in radiating apparatus 2. The light-carrrying core of the fiber is shown as 3 in FIG. 2. The cladding region having a relatively low index of refraction with respect to the core, 3, is shown as 4. The protective sheathing, typically polyethylene or other plastic, is shown as 5. As shown in FIG. 2, the core region extends beyond the cladding and sheathing, typically for a distance of approximately 1.0 to 1.5 millimeters. The region surrounding the exposed core, 6, contains light scattering material, 7. The size of the optical radiator is typically approximately 1 to 3 mm in diameter. However, the uniform spherical light scattering properties depend upon achieving the correct balance of light leaving the fiber core 6, and being scattered by the scattering region 7. Thus, there is no well-defined set of lengths for the various regions. For other purposes, optical radiators of much greater dimension can be fabricated by analogous methods to those disclosed here.

It is well known that light emerges from the exposed end of a cleaved fiber in a highly directional manner, sharply concentrated in the forward direction. Thus, the optical radiator described here must overcome this directionality and cause the light to scatter in an approximately uniform spherical pattern. The basic mode of operation appears to involve a scattering region, 7, large in comparison to the source of light, 6. Thus, when light emerges from the core of the optical fiber, 6, it encounters a strong scattering region, 7. The light is repeatedly scattered in this region, 7, such that, by the time it emerges from region 7, the light has lost all sense of the directionality it originally had while propagating in core 6. In essence, the scattering region 7 must be large enough in comparison to the source of the light 6, the light emerging from core 6 essentially behaves as if it were emanating from a point source. However, the scattering region 7 cannot be too large because, in addition to scattering, all practical scattering materials absorbe a fraction of the light passing through them. Thus, too large a scattering region 7 would cause unacceptable loss of light intensity. Further, as light is absorbed in scattering region 7, the light energy is deposited in region 7 as heat. For excessive absorption, such heating would rapidly cause region 7 to heat beyond the damage threshold of the scattering material. Thus, an appropriate balance of size, light scattering and light absorption must be achieved in constructing the scattering region 7. The procedures described herein are the currently preferred method to achieve this balance.

FIG. 3 illustrates how the present invention would be used in treatment of cancer of the bladder in a male patient. The optical fiber 1 is typically passed through a flexible tube 8, such that the optical radiating apparatus 2 is in the region of the tumor. Laser light is introduced into the end of the fiber opposite apparatus 2 at a location remote from the patient. Light is then radiated into the desired spherical pattern, 9, to effect the treatment.

It is critical to the proper functioning of the apparatus that the optical scattering region be free of air bubbles or other impurities which would tend to cause preferential absorption of the light and, hence, damage to the material. Another critical aspect is the method of coating the optical scattering material, 7, around the tip of the fiber to achieve a reasonably uniform spherical pattern of scattered light. Without a uniform pattern of light, the physician cannot reliably provide the proper dosages to the entire treated area. Thus, another part of the present invention concerns the method of manufacturing this optical radiating apparatus.

A standard optical fiber suitable for transmitting red light (630 nm) is stripped by usual stripping methods exposing at one end thereof a length of core well in excess of the required 1.0 mm to 1.5 mm. The exposed length of core is carefully cleaved to the desired length of approximately 1.0 to 1.5 mm. The tip of the cleaved core is polished flat using, typically, cerium oxide polishing compound although polishing directly with a suitable polishing cloth may also be used.

Having an optical fiber with a short length of exposed, polished core, the scattering region is constructed to produce the desired uniform spherical scattering pattern. A typical scattering medium, which gives preferred performance in this invention, is composed of approximately equal parts powdered quartz (crystobolite) and an optical adhesive. Any of several optical adhesive manufactured by the Norland Company have been tested and found to give good performance.

A critical aspect of the manufacturing process is to apply the scattering medium such that uniform scattering is produced in the region surrounding the exposed core. One useful way to accomplish this is to propagate visible light down the optical fiber during the fabrication process. This light is typically red laser light from a HeNe laser, launched into the fiber from the opposite end from that upon which the optical radiator is being constructed. This light must have suitable intensity to be easily visible to the technician carrying out the fabrication procedure.

Using this test illumination, the technician applies (typically by dipping) the tip of the fiber into the scattering medium. The applied scattering medium is inspected visually by the technician for bright spots or other non-uniformities in the scattering pattern from the test light. Any such imperfections are manually smoothed by the technician before curing. The scattering medium, typically being a mixture of curable optical adhesive and quartz powder, is then cured by exposure to ultraviolet light from a standard source, typically as recommended by the adhesive manufacturer. Further layers of scattering medium are applied, inspected, smoothed and cured as described above until the desired light scattering pattern is obtained.

What is claimed is:

1. A process for manufacturing an apparatus for radiating light of sufficient intensity to cause photodynamic effects in an approximately uniform spherical pattern of approximately $4\pi$ steradians comprising the steps of:
   (a) removing the cladding and sheathing from a region at one end of an optical fiber;
   (b) polishing the smooth, exposed end of the core of said optical fiber exposed by said removal of said cladding and sheathing, making a reasonably smooth, flat surface thereon;
   (c) coating said exposed core and said cladding and sheathing adjacent thereto with a light-scattering medium comprising an approximately equal mixture of powdered quartz and an optical adhesive curable by exposure to ultraviolet radiation, said light-scattering medium applied so as to have uniform scattering power in a spherical pattern around said exposed core and approximately centered thereon by means of the sub-steps;
   (c-i) launching laser light into said optical fiber at the end opposite that end being coated, said light being of sufficient intensity to produce visible rays emanating from the region being coated;
   (c-ii) coating said exposed core region with said light-scattering medium in an approximately spherical light scattering density as determined by an observed uniform intensity in said laser light in a spherical pattern surrounding said core;
   (c-iii) curing said applied coating by exposure to ultraviolet radiation;
   (c-iv) applying a plurality of additional layers of said light-scattering medium by repeating sub-steps (c-ii) and (c-iii).

* * * * *